US009215881B2

(12) United States Patent
Hoshi et al.

(10) Patent No.: US 9,215,881 B2
(45) Date of Patent: Dec. 22, 2015

(54) FERMENTED FOOD AND METHOD FOR PRODUCING SAME

(75) Inventors: Ryotaro Hoshi, Tokyo (JP); Hiroe Utsumi, Tokyo (JP); Akihisa Matsui, Tokyo (JP); Takao Suzuki, Shizuoka (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 2 days.

(21) Appl. No.: 13/877,238

(22) PCT Filed: Sep. 27, 2011

(86) PCT No.: PCT/JP2011/072011
§ 371 (c)(1), (2), (4) Date: May 3, 2013

(87) PCT Pub. No.: WO2012/043532
PCT Pub. Date: Apr. 5, 2012

(65) Prior Publication Data

US 2013/0209412 A1 Aug. 15, 2013

(30) Foreign Application Priority Data

Oct. 1, 2010 (JP) ................................ 2010-223517

(51) Int. Cl.
*A23C 9/12* (2006.01)
*A23C 9/123* (2006.01)
*A23C 9/13* (2006.01)
*A23L 1/30* (2006.01)
*A61K 35/745* (2015.01)

(52) U.S. Cl.
CPC ............ *A23C 9/1203* (2013.01); *A23C 9/1234* (2013.01); *A23C 9/1307* (2013.01); *A23L 1/3002* (2013.01); *A61K 35/745* (2013.01); *A23Y 2300/00* (2013.01); *A23Y 2300/29* (2013.01)

(58) Field of Classification Search
CPC .. A23C 9/1203; A23C 9/1234; A23C 9/1307; A61K 35/745; A23Y 2300/00
USPC .................................. 424/93.4, 780; 426/91
See application file for complete search history.

(56) References Cited

U.S. PATENT DOCUMENTS

| | | | | |
|---|---|---|---|---|
| 3,369,906 | A * | 2/1968 | Chen | 426/239 |
| 5,141,611 | A * | 8/1992 | Ford | 568/717 |
| 2007/0181428 | A1* | 8/2007 | Crowley et al. | 204/520 |
| 2008/0292751 | A1 | 11/2008 | Ogasawara et al. | |
| 2010/0015281 | A1* | 1/2010 | Hoshi et al. | 426/43 |

FOREIGN PATENT DOCUMENTS

| | | | |
|---|---|---|---|
| EP | 1 884 566 | A1 | 2/2008 |
| EP | 1 900 285 | A1 | 3/2008 |
| JP | 2007 202567 | | 8/2007 |
| JP | 2010 11858 | | 1/2010 |
| WO | 2006 126476 | | 11/2006 |
| WO | 2006 129508 | | 12/2006 |

OTHER PUBLICATIONS

Bazinet et al. (2005). Separation and Purification Technology, v41, p. 101-107.*

Samson et al. (2003). Materials and Structures, v36, reprint with 11 pages.*

International Search Report Issued Nov. 8, 2011 in PCT/JP11/72011 Filed Sep. 27, 2011.

Extended European Search Report issued May 14, 2014 in Patent Application No. 11829085.7.

Anonymous, “Bifia”, Database GNPD Mintel, XP-002723508, May 1, 2008, 2 Pages.

* cited by examiner

*Primary Examiner* — Scott Long
*Assistant Examiner* — Sean C Barron
(74) *Attorney, Agent, or Firm* — Oblon, McClelland, Maier & Neustadt, L.L.P.

(57) ABSTRACT

The purpose of the present invention is to provide a technique whereby the flavor of products such as fermented milk that use the *Bifidobacterium* bacteria can be improved while maintaining the effect of the *Rubus suavissimus* S. Lee for improving the viability of the *Bifidobacterium* bacteria. Provided is a fermented food that includes: a *Rubus suavissimus* S. Lee essence obtained as a concentrate through electrodialyzing a *Rubus suavissimus* S. Lee extract added with an inorganic salt; and bacteria of the genus *Bifidobacterium*. Also provided is a method for producing such fermented foods.

9 Claims, No Drawings

FERMENTED FOOD AND METHOD FOR PRODUCING SAME

CROSS REFERENCE TO RELATED APPLICATIONS

The present application is a 35 U.S.C. §371 national stage patent application of International patent application PCT/JP2011/072011, filed on Sep. 27, 2011, published as WO/2012/043532 on Apr. 5, 2012, the text of which is incorporated by reference, and claims the benefit of the filing date of Japanese application no. 2010-223517, filed on Oct. 1, 2010, the text of which is also incorporated by reference.

TECHNICAL FIELD

The present invention relates to fermented foods that contain bacteria of the genus *Bifidobacterium*, and to methods for producing such fermented foods.

BACKGROUND ART

It has been elucidated that bacteria of the genus *Bifidobacterium*, as with the case of lactic acid bacteria such as *Lactobacillus* bacteria, have various effects, including improvement of the intestinal flora, bowel movement, and intestinal tract functions, protection against infections, immunostimulation, and caner prevention. These bacteria are believed to contribute to human health through improvements of the enteral environment.

In order to exhibit such effects, the *Bifidobacterium* bacteria require maintaining a high viable bacterial count in products such as fermented milk. However, because the *Bifidobacterium* bacteria are typically anaerobic, they have poor viability, and rapidly die particularly in the presence of oxygen.

The applicants of the present application have reported adding an extract of sweet tea (*Rubus suavissimus* S. Lee) or the like to products that use the *Bifidobacterium* bacteria such as fermented milk to improve the viability of the *Bifidobacterium* bacteria in such products (Patent Document 1).

However, while adding an extract of *Rubus suavissimus* S. Lee successfully improved the viability of the *Bifidobacterium* bacteria in products such as fermented milk, problem of flavor still remained due to bitterness derived from the *Rubus suavissimus* S. Lee.

LIST OF RELATED ART

Patent Document

Patent Document 1: WO2006/129508

SUMMARY OF THE INVENTION

Problems that the Invention is to Solve

It is accordingly an object of the present invention to provide a technique whereby the flavor of products such as fermented milk that use the *Bifidobacterium* bacteria can be improved while maintaining the effect of the *Rubus suavissimus* S. Lee for improving the viability of the *Bifidobacterium* bacteria.

Means for Solving the Problems

The present inventors conducted intensive studies to solve the foregoing problem, and found that the problem can be solved when the *Rubus suavissimus* S. Lee extract, used in the related art, is added after being electrodialyzed under specified conditions. The present invention has been completed on the basis of this finding.

Specifically, the present invention provides the following.

(1) A fermented food that includes:

a *Rubus suavissimus* S. Lee essence which is obtained as a concentrate through electrodialyzing a *Rubus suavissimus* S. Lee extract added with an inorganic salt; and bacteria of the genus *Bifidobacterium*.

(2) A method for producing a fermented food that contains bacteria of the genus *Bifidobacterium*, the method including blending a *Rubus suavissimus* S. Lee essence, which is obtained as a concentrate through electrodialyzing a *Rubus suavissimus* S. Lee extract added with an inorganic salt, with the fermented food at any stage of fermented food production.

(3) A method for improving the viability of bacteria of the genus *Bifidobacterium*, the method including, blending a *Rubus suavissimus* S. Lee essence, which is obtained as a concentrate through electrodialyzing a *Rubus suavissimus* S. Lee extract added with an inorganic salt, with a fermented food that contains bacteria of the genus *Bifidobacterium*.

(4) A *Rubus suavissimus* S. Lee essence which is obtained as a concentrate through electrodialyzing a *Rubus suavissimus* S. Lee extract added with an inorganic salt.

(5) A method for producing a *Rubus suavissimus* S. Lee essence, the method including electrodialyzing a *Rubus suavissimus* S. Lee extract added with an inorganic salt, and obtaining a concentrate.

(6) A method for improving the flavor of a *Rubus suavissimus* S. Lee extract, the method including electrodialyzing a *Rubus suavissimus* S. Lee extract added with an inorganic salt, and obtaining a concentrate.

Advantage of the Invention

The fermented food of the present invention contains an essence of *Rubus suavissimus* S. Lee which is obtained as a concentrate through electrodialyzing a *Rubus suavissimus* S. Lee extract added with an inorganic salt. The viability of *Bifidobacterium* bacteria contained in the fermented food can thus be improved, and the food does not have the bitterness derived from the *Rubus suavissimus* S. Lee, and is desirable in terms of flavor.

Mode for Carrying Out the Invention

The essence of *Rubus suavissimus* S. Lee which is obtained as a concentrate through electrodialyzing a *Rubus suavissimus* S. Lee extract added with an inorganic salt and contained in the fermented food of the present invention is obtained as follows. First, the leaves and/or stems, preferably the leaves of *Rubus suavissimus* S. Lee (Rosaceae) belonging to the genus *Rubus* of the rose family Rosaceae are extracted with a solvent either directly or after processes such as washing, stripping, drying, and crushing to obtain a *Rubus suavissimus* S. Lee extract.

The solvent used to produce the *Rubus suavissimus* S. Lee extract is not particularly limited, and may be, for example, water, and organic solvents such as lower alcohols of 1 to 5 carbon atoms (such as ethanol), ethyl acetate, glycerine, and propylene glycol. These may be used either alone or as a mixture of two or more. Of these solvents, water and an aqueous solvent such as a mixture of water and lower alcohol are preferred.

The method used to extract the *Rubus suavissimus* S. Lee extract with the solvent is not particularly limited, and is preferably performed by, for example, acid extraction. The acid extraction is performed under acidic conditions of preferably pH 4.0 or less, more preferably pH 3.0 to 4.0. The acid component used to adjust the pH of the solvent in the acid extraction is not particularly limited, as long as it is acidic. Preferred examples of the acid component include organic acids such as citric acid, malic acid, tartaric acid, succinic acid, lactic acid, and acetic acid.

The extraction conditions for the extraction of the *Rubus suavissimus* S. Lee extract with the solvent are not particularly limited, and the extraction is preferably performed, for example, at a temperature of from 0° C. to 100° C., more preferably from 10° C. to 40° C. for about 30 to 60 minutes.

The *Rubus suavissimus* S. Lee extract obtained in this manner is subjected to processes such as filtration and centrifugation as required, and then added with an inorganic salt followed by electrodialysis.

The inorganic salt added to the *Rubus suavissimus* S. Lee extract is not particularly limited, as long as it is a salt formed by an inorganic acid and an inorganic base. Examples of such inorganic salt include one or more selected from potassium salts such as potassium chloride, sodium salts such as sodium chloride, calcium salts such as calcium chloride, and magnesium salts such as magnesium chloride. Of these inorganic salts, magnesium salts are preferred, and magnesium chloride is more preferred. The inorganic salt is added at preferably 0.02 to 0.2 mol/L, more preferably 0.05 to 0.1 mol/L in terms of anhydride. These inorganic salts may be hydrates or anhydrides.

The electrodialyzer used for the electrodialysis may be, such that a cathode and an anode are partitioned by alternately arranging a plurality of cation exchange membranes and a plurality of anion exchange membranes and that includes a cathode chamber, an anode chamber, a plurality of desalinating chambers, and a plurality of concentration chambers. Such an electrodialyzer produces a concentrated liquid of an ionic substance (concentrate), and a liquid free of the ionic substance (desalinated liquid). Specifically, the concentration chambers occupy portions parted by the anode-side cation exchange membranes and the cathode-side anion exchange membranes, and the liquid refluxed into the concentration chambers is the concentrate. The desalinating chambers occupy portions parted by the anode-side anion exchange membranes and the cathode-side cation exchange membranes, and the liquid refluxed into the desalinating chambers is the desalinated liquid. Commercially available electrodialyzers, for example, the Acilyzer (available from Astom Co., Ltd.) may also be used.

The *Rubus suavissimus* S. Lee essence of the present invention can be obtained by collecting the concentrate which is obtained through electrodialysis performed by refluxing the *Rubus suavissimus* S. Lee extract added with an inorganic salt into the desalinating chambers of the electrodialyzer, and refluxing water or the like into the concentration chambers. The electrodialysis conditions are not particularly limited. For example, the electrodialysis may be performed by refluxing water into the concentration chambers in amounts equivalent to 5 to 50 mass % (hereinafter, simply "%"), preferably 10 to 30% of the *Rubus suavissimus* S. Lee extract, followed by applying a voltage of 10 to 200 V, preferably 50 to 100 V across the cathode and the anode, and passing a current of 10 to 200 A, preferably 50 to 100 A until the electrical conductivities of the desalinating chambers reach equilibrium (2 millisiemens per centimeter (mS/cm)). The concentrate can then be collected. Aside from water, the liquid refluxed into the concentration chambers may be, for example, an electrolytic solution such as brine, and citric acid in water.

The *Rubus suavissimus* S. Lee essence may be used either as it is after the electrodialysis, or as a concentrate after being purified and concentrated through ultrafiltration, centrifugation, or the like, or as a powdery form after drying the concentrate by spray drying, freeze drying, or the like.

The amount of the *Rubus suavissimus* S. Lee essence used in the fermented food of the present invention is not particularly limited. For example, in the case of a *Rubus suavissimus* S. Lee essence of 12 Brix, the concentration of the essence in the fermented food is 0.001 to 0.1%, preferably 0.001 to 0.05%, more preferably 0.002 to 0.02%. Note that the Brix value is a measured value obtained from, for example, a digital refractometer such as RX-7000α (Atago Co., Ltd.).

The *Bifidobacterium* bacteria used for the production of the fermented food of the present invention and contained therein are not particularly limited, as long as they are microorganisms that belong to the genus *Bifidobacterium*. Preferred examples include members of major human intestinal flora such as *Bifidobacterium breve, Bifidobacterium longum, Bifidobacterium infantis, Bifidobacterium adolescentis, Bifidobacterium bifidum, Bifidobacterium catenulatum, Bifidobacterium pseudocatenulatum*, and *Bifidobacterium angulatum*, and *Bifidobacterium gallicum* isolated or derived from the human intestines, and *Bifidobacterium lactis* and *Bifidobacterium animalis* used for food. Particularly preferred among these *Bifidobacterium* bacteria from the standpoint of the effect of improving viability when used together with the extract are *Bifidobacterium breve, Bifidobacterium bifidum*, and *Bifidobacterium longum*, and, more preferred are *Bifidobacterium breve* YIT12272 (FERM P-21917, deposited Feb. 16, 2010), *Bifidobacterium breve* YIT4065 (FERM BP-6223, deposited Feb. 29, 1996), *Bifidobacterium breve* YIT10001 (FERM BP-8205, deposited Aug. 14, 2001), *Bifidobacterium bifidum* YIT4007 (FERM BP-791, deposited: May 1, 1981), and *Bifidobacterium bifidum* YIT10347 (FERM BP-10613, deposited Jun. 23, 2005).

The effect of improving the viability of the *Bifidobacterium* bacteria in the fermented food of the present invention with use of the *Rubus suavissimus* S. Lee essence can be further improved by containing microorganisms other than the *Bifidobacterium* bacteria, particularly lactic acid bacteria in the fermented food with the *Bifidobacterium* bacteria. Examples of such microorganisms include lactic acid bacteria of the genus *Lactobacillus* (such as *Lactobacillus casei, Lactobacillus acidophilus, Lactobacillus helveticus, Lactobacillus salivarius, Lactobacillus gasseri, Lactobacillus fermentum, Lactobacillus reuteri, Lactobacillus crispatus, Lactobacillus delbrueckii* subsp. *bulgaricus, Lactobacillus delbueckii* subsp. *delbueckii*, and *Lactobacillus johnsonii*), the genus *Streptococcus* (such as *Streptococcus thermophilus*), the genus *Lactococcus* (such as *Lactococcus lactis* subsp. *lactis, Lactococcus lactis* subsp. *cremoris, Lactococcus plantarum*, and *Lactococcus raffinolactis*), and the genus *Enterococcus* (such as *Enterococcus faecalis*, and *Enterococcus faecium*). Preferred among these lactic acid bacteria are *Lactococcus lactis* and/or *Streptococcus thermophilus*, and, more preferably *Lactococcus lactis* YIT2027 (FERM BP-6224, deposited Feb. 10, 1997) and/or *Streptococcus thermophilus* YIT2021 (FERM BP-7537, deposited Nov. 1, 1996).

The bacteria listed above with the deposit dates are deposited at The National Institute of Advanced Industrial Science and Technology, International Patent Organism Depositary (1-chuo, dai-6, 1-1, Higashi, Tsukuba-shi, Ibaraki 305-8566, Japan).

The effect of improving the viability of the *Bifidobacterium* bacteria with the *Rubus suavissimus* S. Lee essence in the fermented food of the present invention can greatly improve when the *Bifidobacterium* bacterial count in the fermented food at the time of the production of the fermented food is $1\times10^7$ cfu/ml or more, particularly $1\times10^8$ cfu/ml or more.

The fermented food of the present invention can be produced according to known methods of producing fermented food that uses the *Bifidobacterium* bacteria, except for adding the *Rubus suavissimus* S. Lee essence at any stage of the production of the fermented food that uses the *Bifidobacterium* bacteria. In one exemplary producing method of the fermented food, the *Rubus suavissimus* S. Lee essence is added before or after sterilizing a powdered skim milk solution, and the *Bifidobacterium* bacteria or other desired microorganisms are inoculated and cultured. The product is then homogenized to obtain a fermented milk base, and a separately prepared syrup solution is added and mixed. Finally, a flavor or other ingredients are added to obtain the final product. In another exemplary method, the *Bifidobacterium* bacteria or other desired microorganisms are inoculated and cultured in a sterilized powdered skim milk solution. The product is then homogenized to obtain a fermented milk base, and a separately prepared syrup solution and the *Rubus suavissimus* S. Lee essence are added and mixed. Finally, a flavor or other ingredients are added to obtain the final product. When the fermented food of the present invention contains the *Bifidobacterium* bacteria and the lactic acid bacteria, a mixed culture of the *Bifidobacterium* bacteria and the lactic acid bacteria may be used for the production of the fermented food, or these bacteria may be separately cultured, and then mixed and used for the production of the fermented food.

As used herein, "fermented food" encompasses products specified by the ministerial ordinance for milk products, including drinks (such as fermented milk, and dairy lactic acid bacteria beverages), hard yogurt, soft yogurt, plain yogurt, kefir, and cheese. The fermented food of the present invention also encompasses various types of foods and beverages that use lactic acid bacteria, such as fermented milk, lactic acid bacteria beverage, kefir, and cheese of varieties such as a plain type, a flavored type, a fruit type, a sweet type, a soft type, a drink type, a solid (hard) type, and a frozen type.

The fermented food of the present invention may contain sweeteners such as syrups, and other food materials, for example, any components such as various sugars, thickeners, emulsifiers, and various vitamins, as required. Specific examples of such food materials include sugars such as sucrose, glucose, fructose, palatinose, trehalose, lactose, xylose, and maltose; sugar alcohols such as sorbitol, xylitol, erythritol, lactitol, Palatinit, reduced starch syrup, and reduced maltose starch syrup; high sweeteners such as aspartame, thaumatin, sucralose, acesulfame K, and stevia; various thickeners (stabilizers) such as agar, gelatin, carrageenan, guar gum, xanthan gum, pectin, locust bean gum, gellan gum, carboxymethyl cellulose, soy polysaccharides, and propylene glycol alginate; emulsifiers such as sucrose fatty acid ester, glycerin fatty acid ester, polyglycerin fatty acid ester, sorbitan fatty acid ester, and lecithin; milk fats such as cream, butter, and sour cream; acidulants such as citric acid, lactic acid, acetic acid, malic acid, tartaric acid, and gluconic acid; vitamins such as vitamin A, vitamin B, vitamin C, and vitamin E; minerals such as calcium, magnesium, zinc, iron, and manganese; and various flavors of yogurt, berry, orange, quince, perilla, citrus, apple, mint, grape, apricot, pear, custard cream, peach, melon, banana, tropical products, herb, black tea, and coffee.

The fermented food of the present invention obtained as above can maintain a *Bifidobacterium* bacteria viability rate of 20% or more, and/or a viable bacterial count of $1.5\times10^8$ cfu/ml, preferably $2\times10^8$ cfu/ml even after being stored at 10° C. for 21 days, and the food does not have the bitterness derived from the *Rubus suavissimus* S. Lee, and is desirable in terms of flavor. The viability rate can be determined according to the method described in the Examples below.

EXAMPLES

The present invention is described below in more detail using Examples. It should be noted, however, that the present invention is in no way limited by the following Examples.

Reference Example 1

Production of *Rubus suavissimus* S. Lee Extract

After treating leaves of *Rubus suavissimus* S. Lee by processes such as comminution, water was added in an amount 15 times the amount of the *Rubus suavissimus* S. Lee leaves. After adjusting the pH to 3.8 by addition of citric acid in an amount equivalent to 5% of the *Rubus suavissimus* S. Lee leaves, the sample was extracted at 20° C. for 60 minutes, and the resulting extract was quintuple-concentrated with an evaporator to obtain a *Rubus suavissimus* S. Lee extract of 13 Brix.

Example 1

Production of *Rubus suavissimus* S. Lee Essence (1)

After treating leaves of *Rubus suavissimus* S. Lee by processes such as comminution, water was added in an amount 15 times the amount of the *Rubus suavissimus* S. Lee leaves. After adjusting the pH to 3.8 by addition of citric acid in an amount equivalent to 5% of the *Rubus suavissimus* S. Lee leaves, the sample was extracted at 20° C. for 60 minutes. Magnesium chloride hexahydrate was then added to the extract so that the magnesium chloride concentration was 0.05 mol/L. The mixture was charged into the desalinating chambers of an electrodialyzer (electrodialysis membrane: AC220-50; Microacilyzer S-3, Astom), and water equivalent to 17% of the extract was charged into the concentration chambers. The electrodialysis process was continued until the electrical conductivities of the desalinating chambers reached equilibrium (2 millisiemens per centimeter (mS/cm)) , and the concentrate was collected. The concentrate was further quintuple-concentrated with an evaporator, and a *Rubus suavissimus* S. Lee essence 1 of 12 Brix was obtained.

Example 2

Production of Dairy Product (1)

0.2% *Rubus suavissimus* S. Lee essence 1 prepared in Example 1 was added to a 20% powdered skim milk medium prepared as a basal medium, and was heat sterilized at 120° C. for 3 seconds to prepare a culture medium. The medium was inoculated with a *Bifidobacterium breve* YIT12272 starter (1%), a *Lactococcus lactis* YIT2027 starter (0.1%), and a *Streptococcus thermophilus* YIT2021 starter (0.01%), and cultured at 37° C. for 24 hours to obtain a culture. The culture was homogenized under 15 MPa, and 60 parts by mass of a 10% sugar solution which was sterilized at 100° C. for 5 minutes was added to 40 parts by mass of the homogenized culture. 0.1% yogurt flavoring ingredient (product of Kabushiki Kaisha Yakult Material) was then added to produce a dairy product. For comparison, a diary product was produced in the same manner as above, except for using a medium prepared by adding a *Rubus suavissimus* S. Lee extract (0.2%) to the basal medium, instead of the *Rubus suavissimus* S. Lee essence 1. The concentrations of the *Rubus suavissimus* S. Lee essence 1 and the *Rubus suavissimus* S. Lee extract in the dairy products were 0.08%.

The viable bacterial count (cfu/ml) in the dairy product was measured at the production and after the product was stored at 10° C. for 21 days, using a TOS medium (Yakult Pharmaceutical Industry Co., Ltd.). The viability rate of the *Bifidobacterium* bacteria was also determined according to the equation below. The results are presented in Table 1. The dairy product was also evaluated for flavor by three trained panelists according to the following criteria. The results are presented in Table 1.

Viability rate (%)=viable bacterial count after storage÷viable bacterial count at production×100 Equation 1

| Flavor Evaluation Criteria | |
|---|---|
| Score | Description |
| 5: | No bitterness |
| 4: | Almost no bitterness |
| 3: | Slight bitterness |
| 2: | Bitter |
| 1: | Strong bitterness |

TABLE 1

| Additive | Viable cell count at production (cfu/ml) | Viable cell count after storage (cfu/ml) | Viability rate (%) | Flavor |
|---|---|---|---|---|
| None | $8.2 \times 10^8$ | $1.3 \times 10^8$ | 16 | 5 |
| *Rubus suavissimus* S. Lee extract | $8.9 \times 10^8$ | $3.6 \times 10^8$ | 40 | 2 |
| *Rubus suavissimus* S. Lee essence 1 | $9.0 \times 10^8$ | $3.8 \times 10^8$ | 42 | 5 |

As is clear from Table 1, both the dairy products containing the *Rubus suavissimus* S. Lee extract and the *Rubus suavissimus* S. Lee essence 1 had increased viability rates for the *Bifidobacterium* bacteria compared to the diary product prepared with only the basal medium. It was also found that the *Rubus suavissimus* S. Lee essence 1 produced a good flavor without bitterness in the dairy product, even though it was added in an amount that improves the viability rate more than the *Rubus suavissimus* S. Lee extract.

Example 3

Production of *Rubus suavissimus* S. Lee Essence (2)

*Rubus suavissimus* S. Lee essences 2 to 5 were produced in the same manner as in Example 1, except that sodium chloride, potassium chloride, calcium chloride dihydrate, or tripotassium citrate monohydrate was used in place of the magnesium chloride hexahydrate, and was added to make the anhydride concentration 0.05 mol/L.

Example 4

Production of Dairy Product (2)

Dairy products were obtained in the same manner as in Example 2, except that the *Rubus suavissimus* S. Lee essences 2 to 5 produced in Example 3 were used in place of the *Rubus suavissimus* S. Lee essence 1 in the same amount. These dairy products were measured for viable bacterial count at the production and after storage at 10° C. for 21 days in the same manner as in Example 2. The viability rate was also determined, and the flavor was evaluated. The results are presented in Table 2.

TABLE 2

| Additive | Inorganic salt or organic salt | Viable cell count at production (cfu/ml) | Viable cell count after storage (cfu/ml) | Viability rate (%) | Flavor |
|---|---|---|---|---|---|
| None | None | $8.2 \times 10^8$ | $1.3 \times 10^8$ | 16 | 5 |
| *Rubus suavissimus* S. Lee essence 1 | Magnesium chloride | $9.0 \times 10^8$ | $3.8 \times 10^8$ | 42 | 5 |
| *Rubus suavissimus* S. Lee essence 2 | Sodium chloride | $7.8 \times 10^8$ | $1.3 \times 10^8$ | 17 | 4 |
| *Rubus suavissimus* S. Lee essence 3 | Potassium chloride | $8.5 \times 10^8$ | $1.9 \times 10^8$ | 22 | 5 |
| *Rubus suavissimus* S. Lee essence 4 | Calcium chloride | $8.3 \times 10^8$ | $2.5 \times 10^8$ | 30 | 4 |
| *Rubus suavissimus* S. Lee essence 5 | Tripotassium citrate | $7.7 \times 10^8$ | $1.2 \times 10^8$ | 16 | 5 |

As is clear from Table 2, the *Rubus suavissimus* S. Lee essence obtained by adding magnesium chloride had superior viability improving effect than the *Rubus suavissimus* S. Lee essences obtained by adding other salts. The viability improving effect was not obtained by addition of the organic salt tripotassium citrate.

Example 5

Production of *Rubus suavissimus* S. Lee Essence (3)

*Rubus suavissimus* S. Lee essences 6 to 10 were produced in the same manner as in Example 1, except that magnesium chloride hexahydrate was used so as to make the magnesium chloride concentration 0.01, 0.02, 0.1, 0.2, or 0.5 mol/L, respectively, instead of 0.05 mol/L.

Example 6

Production of Dairy Product (3)

Dairy products were obtained in the same manner as in Example 2, except that the *Rubus suavissimus* S. Lee essences 6 to 10 produced in Example 5 were used in place of the *Rubus suavissimus* S. Lee essence 1 in the same amount. These dairy products were measured for viable bacterial count at the production and after storage at 10° C. for 21 days in the same manner as in Example 2. The viability rate was also determined, and the flavor was evaluated. The results are presented in Table 3.

TABLE 3

| Additive | Amount of magnesium chloride added (mol/L) | Viable cell count at production (cfu/ml) | Viable cell count after storage (cfu/ml) | Viability rate (%) | Flavor |
|---|---|---|---|---|---|
| None | 0 | $8.2 \times 10^8$ | $1.3 \times 10^8$ | 16 | 5 |
| *Rubus suavissimus* S. Lee essence 6 | 0.01 | $8.5 \times 10^8$ | $1.9 \times 10^8$ | 22 | 5 |
| *Rubus suavissimus* S. Lee essence 7 | 0.02 | $9.0 \times 10^8$ | $2.8 \times 10^8$ | 31 | 5 |
| *Rubus suavissimus* S. Lee essence 1 | 0.05 | $9.0 \times 10^8$ | $3.8 \times 10^8$ | 42 | 5 |
| *Rubus suavissimus* S. Lee essence 8 | 0.1 | $8.8 \times 10^8$ | $3.7 \times 10^8$ | 42 | 5 |
| *Rubus suavissimus* S. Lee essence 9 | 0.2 | $8.4 \times 10^8$ | $3.7 \times 10^8$ | 44 | 4 |
| *Rubus suavissimus* S. Lee essence 10 | 0.5 | $9.0 \times 10^8$ | $3.8 \times 10^8$ | 42 | 3 |

As is clear from Table 3, the viability improving effect for the *Bifidobacterium* bacteria had the tendency to greatly increase with the use of the *Rubus suavissimus* S. Lee essences obtained as concentrates in the electrodialysis performed by adding magnesium chloride to the *Rubus suavissimus* S. Lee extract, particularly the *Rubus suavissimus* S. Lee essences that contained magnesium chloride at 0.02 mol/L or more. It was also found that the addition of magnesium chloride does not have adverse effects on flavor when added at 0.2 mol/L or less. The viability improving effect was particularly prominent, and the flavor was desirable in samples that contained magnesium chloride at 0.05 to 0.1 mol/L.

Example 7

Production of Dairy Product (4)

The *Rubus suavissimus* S. Lee essence 1 prepared in Example 1 was added to a 20% powdered skim milk medium at 0.01, 0.02, 0.05, 0.1, 0.2, or 0.5%, and was heat sterilized at 120° C. for 3 seconds to prepare a culture medium. Each medium was inoculated with a *Bifidobacterium breve* YIT12272 starter (1%) and a *Lactococcus lactis* YIT2027 starter (0.01%), and cultured at 37° C. for 24 hours to obtain culture A. Separately, a 16% powdered skim milk medium was inoculated with a Streptococcus thermophilus YIT2021 starter (0.5%), and cultured at 37° C. for 24 hours to obtain culture B. Further, reduced maltose starch syrup (8%), polydextrose (4%), galactooligosaccharide liquid sugar (4%), pectin (0.5%), collagenpeptide (0.2%), vitamin B preparation (0.05%), sucralose (0.007%), emulsified iron (iron pyrophosphate; 0.6%) were dissolved in water, and sterilized at 121° C. for 3 seconds to obtain a syrup.

Culture A and culture B were each homogenized under 15 MPa, and 10 parts by mass of culture A and 40 parts by mass of culture B were mixed with 50 parts by mass of the syrup. Then, three different yogurt flavoring ingredients (Ogawa & Co., Ltd., T. Hasegawa Co., Ltd., and Yakult Material) were added to the mixture at a total of 0.1% to produce dairy products. The concentrations of the *Rubus suavissimus* S. Lee essence 1 in these dairy products were 0.001, 0.002, 0.005, 0.01, 0.02, and 0.05%.

The dairy products were measured for viable bacterial count for *Bifidobacterium breve* at the production and after a 10° C., 21-day storage period in the same manner as in Example 2. The viability rate was also determined, and the flavor was evaluated. The results are presented in Table 4.

TABLE 4

| | Concentration of *Rubus suavissimus* S. Lee essence 1 in dairy product | Viable cell count at production (cfu/ml) | Viable cell count after storage (cfu/ml) | Viability rate (%) | Flavor |
|---|---|---|---|---|---|
| Basal medium | 0 | $8.2 \times 10^8$ | $1.3 \times 10^8$ | 16 | 5 |
| Culture medium | 0.001 | $8.4 \times 10^8$ | $2.0 \times 10^8$ | 24 | 5 |
| Culture medium | 0.002 | $8.1 \times 10^8$ | $2.4 \times 10^8$ | 30 | 5 |
| Culture medium | 0.005 | $8.5 \times 10^8$ | $3.1 \times 10^8$ | 36 | 5 |
| Culture medium | 0.01 | $8.9 \times 10^8$ | $3.4 \times 10^8$ | 38 | 5 |
| Culture medium | 0.02 | $9.0 \times 10^8$ | $3.8 \times 10^8$ | 42 | 5 |
| Culture medium | 0.05 | $8.7 \times 10^8$ | $3.3 \times 10^8$ | 38 | 3 |

As is clear from Table 4, adding the *Rubus suavissimus* S. Lee essence achieved the viability improving effect for the *Bifidobacterium* bacteria without having almost any adverse effects on the flavor of the dairy product. Particularly, it was found that adding the *Rubus suavissimus* S. Lee essence (12 Brix) at 0.002 to 0.02% concentrations in the dairy products produces dairy products having high viability and a desirable flavor.

Example 8

Production of Dairy Product (5)

Dairy products were produced in the same manner as in Example 7, except that *Bifidobacterium breve* YIT4065 was used instead of the *Bifidobacterium breve* YIT12272. As with the case of the dairy products obtained in Example 7, the dairy products had an improved viability improving effect for the *Bifidobacterium* bacteria by addition of the *Rubus suavissimus* S. Lee essence, without having almost any adverse effect on the flavor of the dairy products.

Example 9

Production of Dairy Product (6)

Dairy products were produced in the same manner as in Example 7, except that *Bifidobacterium breve* YIT10001 was used instead of the *Bifidobacterium breve* YIT12272. As with the case of the dairy products obtained in Example 7, the dairy products had an improved viability improving effect for the *Bifidobacterium* bacteria by addition of the *Rubus suavissimus* S. Lee essence, without having almost any adverse effect on the flavor of the dairy products.

Example 10

Production of Dairy Product (7)

Dairy products were produced in the same manner as in Example 7, except that *Bifidobacterium bifidum* YIT4007 was used instead of the *Bifidobacterium breve* YIT12272. As with the case of the dairy products obtained in Example 7, the dairy products had an improved viability improving effect for the *Bifidobacterium* bacteria by addition of the *Rubus suavissimus* S. Lee essence, without having almost any adverse effect on the flavor of the dairy products.

Example 11

Production of Dairy Product (8)

Dairy products were produced in the same manner as in Example 7, except that *Bifidobacterium bifidum* YIT10347 was used instead of the *Bifidobacterium breve* YIT12272. As with the case of the dairy products obtained in Example 7, the dairy products had an improved viability improving effect for the *Bifidobacterium* bacteria by addition of the *Rubus suavissimus* S. Lee essence, without having almost any adverse effect on the flavor of the dairy products.

INDUSTRIAL APPLICABILITY

The fermented food of the present invention can provide various effects of the *Bifidobacterium* bacteria, and can contribute to human health.

The invention claimed is:

1. A fermented milk that comprises:

skim milk, a yogurt flavoring ingredient, a *Rubus suavissimus* S. Lee essence which is a concentrate obtained by adding water to leaves of *Rubus suavissimus* S. Lee, extracting the leaves at pH 4.0 or below to obtain a *Rubus suavissimus* S. Lee extract, adding 0.02 to 0.2 mol/L of magnesium chloride to the extract, charging the mixture into the desalinating chambers of an electrodialyzer, charging water into the concentration chambers, and conducting the electrodialysis process until the electrical conductivities of the desalinating chambers reach equilibrium; and bacteria of the genus *Bifidobacterium*, wherein a *Bifidobacterium* bacteria viability rate is at least 20% after being stored at 10° C. for 21 days.

2. A method for producing the fermented milk of claim 1, the method comprising blending the *Rubus suavissimus* S. Lee essence with the skim milk, yogurt flavoring ingredient, and bacteria of the genus *Bifidobacterium* at any stage of fermented milk production.

3. A *Rubus suavissimus* S. Lee essence which is a concentrate obtained by adding water to leaves of *Rubus suavissimus* S. Lee, extracting the leaves at pH 4.0 or below to obtain a *Rubus suavissimus* S. Lee extract, adding 0.02 to 0.2 mol/L of magnesium chloride to the extract, charging the mixture into the desalinating chambers of an electrodialyzer, charging water into the concentration chambers, and conducting the electrodialysis process until the electrical conductivities of the desalinating chambers reach equilibrium.

4. A method for producing a *Rubus suavissimus* S. Lee essence comprising the method comprising adding water to leaves of *Rubus suavissimus* S. Lee, extracting the leaves at pH 4.0 or below to obtain a *Rubus suavissimus* S. Lee extract, adding 0.02 to 0.2 mol/L of magnesium chloride to the extract, charging the mixture into the desalinating chambers of an electrodialyzer, charging water into the concentration chambers, and conducting the electrodialysis process until the electrical conductivities of the desalinating chambers reach equilibrium.

5. A method for improving the viability of bacteria of the genus *Bifidobacterium*, the method comprising blending the *Rubus suavissimus* S. Lee of claim 3 with a fermented food that contains bacteria of the genus *Bifidobacterium*.

6. The fermented milk according to claim 1, wherein the is magnesium chloride is added in an amount ranging from 0.05 to 0.1 mol/L.

7. The fermented milk according to claim 1, comprising 0.001 to 0.1% of the *Rubus suavissimus* S. Lee essence on a basis of 12 Brix.

8. The fermented milk according to claim 1, wherein a viable bacterial count is at least $1.5\times10^8$ cfu/ml after being stored at 10° C. for 21 days.

9. The fermented milk according to claim 1, wherein a viable bacterial count is at least $2\times10^8$ cfu/ml after being stored at 10° C. for 21 days.

* * * * *